US011230563B2

(12) United States Patent
Cruse et al.

(10) Patent No.: US 11,230,563 B2
(45) Date of Patent: Jan. 25, 2022

(54) METHOD OF STABILIZING IMINO-FUNCTIONAL SILANE

(71) Applicant: Momentive Performance Materials Inc., Waterford, NY (US)

(72) Inventors: Richard W Cruse, Yorktown Heights, NY (US); Matthew Pinnow, Millwood, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 16/574,704

(22) Filed: Sep. 18, 2019

(65) Prior Publication Data

US 2020/0010490 A1 Jan. 9, 2020

Related U.S. Application Data

(62) Division of application No. 15/649,919, filed on Jul. 14, 2017, now Pat. No. 10,457,697.

(60) Provisional application No. 62/362,741, filed on Jul. 15, 2016.

(51) Int. Cl.
| | |
|---|---|
| *C07F 7/18* | (2006.01) |
| *C07F 7/20* | (2006.01) |
| *C01D 1/02* | (2006.01) |
| *C01D 1/04* | (2006.01) |
| *C07C 31/04* | (2006.01) |

(52) U.S. Cl.
CPC .............. *C07F 7/1804* (2013.01); *C07F 7/20* (2013.01); *C01D 1/02* (2013.01); *C01D 1/04* (2013.01); *C07C 31/04* (2013.01)

(58) Field of Classification Search
None
See application file for complete search history.

(56) References Cited

U.S. PATENT DOCUMENTS

| | | | |
|---|---|---|---|
| 2,498,419 A * | 2/1950 | Haury | ........................... 564/279 |
| 2,942,019 A | 6/1960 | Pike et al. | |
| 3,424,656 A | 1/1969 | Berger | |
| 3,681,420 A | 8/1972 | Brown et al. | |
| 4,832,748 A * | 5/1989 | Tawara | .............. C08G 59/4042 |
| | | | 106/287.11 |
| 5,134,234 A | 7/1992 | Parrinello et al. | |
| 5,739,201 A | 4/1998 | Ugai et al. | |
| 6,586,612 B2 | 7/2003 | Gedon et al. | |
| 6,998,499 B2 | 2/2006 | Gedon et al. | |
| 7,906,673 B2 | 3/2011 | Burckhardt | |
| 7,923,572 B2 | 4/2011 | Taniguchi et al. | |
| 8,877,955 B2 | 11/2014 | Burckhardt | |
| 2013/0281562 A1 | 10/2013 | Burckhardt | |
| 2015/0269973 A1 | 9/2015 | Sugita | |
| 2015/0380094 A1 | 12/2015 | Nagashima | |

FOREIGN PATENT DOCUMENTS

WO 20090043599 A1 4/2009

OTHER PUBLICATIONS

Wikipedia, "Aldol Codensation" dated Jul. 7, 2016.
International Search Report and Written Opinion for PCT/US2017/042088 dated Oct. 20, 2017.

* cited by examiner

*Primary Examiner* — Clinton A Brooks
(74) *Attorney, Agent, or Firm* — James C. Abruzzo

(57) ABSTRACT

A method of stabilizing imino-functional silane involving adding thereto at least one Brønsted-Lowry base to inhibit, suppress or prevent the addition reactions of the imino-functional silane with itself to form a imino- and amino-functional silane and the subsequent deamination reactions to form conjugated carbon-carbon double bond-containing imino-functional silanes and stabilized imino-functional silanes containing the at least one Brønsted-Lowry base.

15 Claims, No Drawings

METHOD OF STABILIZING IMINO-FUNCTIONAL SILANE

CROSS REFERENCE TO RELATED APPLICATION

This application is a divisional application of U.S. patent application Ser. No. 15/649,919 filed on Jul. 14, 2017, which claims the benefit of provisional U.S. Patent Application Ser. No. 62/362,741 filed Jul. 15, 2016, the entire contents of which are incorporated by reference herein.

FIELD OF THE INVENTION

This invention relates to imino-functional silanes and, more particularly, to a method of purifying and/or for the post-production treatment of imino-functional silanes to inhibit addition reactions on the imino-functional silanes to produce an imino- and amino-functional silane and the subsequent deamination reaction to produce a conjugated carbon-carbon double bond containing imino-functional silane that occurs therein during storage.

BACKGROUND OF THE INVENTION

Iminosilanes of various kinds are known in the art and are known to be useful as, among others, intermediates for the production of amine-containing compounds and silylated polymers, adhesion promoters for coating, adhesive and sealants and as coupling agents for mineral filled composites.

Among the known imino-functional silanes and methods for their preparation are the aldimino-functional silanes, ketimino-functional silanes and preparative methods described in U.S. Pat. No. 2,942,019; the N,N'-bis[(tri(substituted)silylalkylene]-1,4-xylene-a,a'-diimines and preparative methods described in U.S. Pat. No. 3,681,420; the imino-functional silanes and preparative methods utilizing isocyanates described in U.S. Pat. No. 5,134,234; the aldimino-functional silanes and ketimino-functional silanes and preparative methods described in U.S. Pat. No. 5,739,201; the imino-functional silanes and amine exchange preparative methods described in U.S. Pat. Nos. 6,586,612 and 6,998,449; the aldimino-functional silanes and preparative methods described in U.S. Pat. Nos. 7,906,673 and 8,877,955; the ketimino-functional silanes and preparative methods described in U.S. Pat. No. 7,923,572; and, the amino-functional silanes ("activated silanes") and preparative methods described in WO2009/043599. The contents of each of these patent publications are incorporated herein in their entirety.

Imino-functional silanes undergo addition reactions to form imido- and amino-functional silanes and these imido- and amino-functional silanes may further undergo deamination reactions to form conjugated carbon-carbon double bond containing imino-functional silanes. These undesirable reaction products reduce the content of the desired imino-functional silanes, may generate color making them unsuitable as intermediates or adhesion promoters for clear compositions and curtail their storage stability. Because of these adverse effects on product purity and storage stability, a need has arisen for a method of inhibiting, suppressing or preventing the reactions of imino-functional silanes with themselves and the subsequent deamination reactions.

SUMMARY OF THE INVENTION

In accordance with the present invention, there is provided a method of stabilizing imino-functional silane comprising:

a) adding a Brønsted-Lowry base to an imino-functional silane; and, b) mixing the imino-functional silane with the at least one Brønsted-Lowry base to provide stabilized imino-functional silane.

Although not intended to be bound by theory, it is believed that the untreated imino-functional silane contains at least one acidic proton source and in the presence thereof and increasingly over time, the imino-functional silane undergoes reaction with itself to form undesirable and unwanted addition and deamination reactions. The reactants used in the process for preparing the imino-functional silane, such as aldehydes, ketones and/or aminosilanes, may contain a source of protons (H+), e.g., a Brønsted-Lowry acid. Even in trace amounts, these Brønsted-Lowry acids can catalyze the aforementioned undesirable imino-functional silane addition and deamination reactions thereby generating as a reaction product, a conjugated carbon-carbon double bond containing imino-functional silane and as by-product, the amino-functional silane that was originally employed as reactant in the preparation of the desired imino-functional silane. Such undesirable reactions reduce the amount of desired imino-functional silane over time, e.g., during storage, and can result in a significant loss of imino-functional silane product accompanied by a wasteful buildup of conjugated carbon-carbon double bond containing imino-functional silane and amino-functional silane impurities.

The method of the invention when applied to freshly prepared iminosilane product effectively inhibits or prevents addition and deamination reactions of the iminosilane from occurring, or if some addition and deamination reactions have already taken place, prevents such reactions from proceeding further. In one embodiment, the method of the invention therefore preserves, or substantially preserves, the original content of desired imino-functional silane product, suppresses or eliminates the generation of wasteful addition and deamination reaction products and greatly increases the storage stability of the treated imino-functional silane product.

DETAILED DESCRIPTION OF THE INVENTION

In the specification and claims herein, the following terms and expression are to be understood as having the hereinafter indicated meanings.

The singular forms "a," "an" and "the" include the plural, and reference to a particular numerical value includes at least that particular value unless the context clearly dictates otherwise.

All methods described herein may be performed in any suitable order unless otherwise indicated herein or otherwise clearly contradicted by context. The use of any and all examples or exemplary language (e.g., "such as") provided herein is intended merely to better illuminate the invention and does not pose a limitation on the scope of the invention unless otherwise claimed.

No language in the specification should be construed as indicating any non-claimed element as essential to the practice of the invention.

As used herein, the terms "comprising," "including," "containing," "characterized by" and grammatical equivalents thereof are inclusive or open-ended terms that do not exclude additional, unrecited elements or method steps, but will also be understood to include the more restrictive terms "consisting of" and "consisting essentially of."

Composition percentages are given in weight percent unless otherwise indicated.

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression, "proton source", means a compound that can release a proton.

The expression "Brønsted-Lowry acid" shall be understood herein to apply to any compound that can transfer a proton to any other compound, i.e., to a proton donor. A proton is a nuclear particle with a unit positive electrical charge; it is represented by the symbol $H^+$ as it constitutes the nucleus of a hydrogen atom.

The expression "Brønsted-Lowry base" shall be understood herein to apply to any compound that accepts a proton, i.e., to a proton acceptor.

The expression "conjugated carbon-carbon double bond containing imino-functional silane" shall be understood herein to mean any molecule containing the bond sequence C=C—C=N where C=C denotes a carbon-carbon double bond and C=N denotes a carbon-nitrogen double bond, i.e., an imino group.

The term "hydrocarbon group" means any hydrocarbon compound containing only hydrogen and carbon atoms from which one or more hydrogen atoms has been removed. Hydrocarbon group is inclusive of alkyl, alkenyl, alkynyl, alkylene, cycloalkyl, cycloalkenyl, cycloalkynyl, aryl, aralkyl and arenyl.

A "heterocarbon group" means a hydrocarbon group containing one or more heteroatoms.

The term "heteroatom" means any of the Group 13-17 elements except carbon and includes, for example, oxygen, nitrogen, silicon, sulfur, phosphorus, fluorine, chlorine, bromine and iodine.

The term "alkyl" means any monovalent, saturated straight chain or branched chain hydrocarbon group; the term "alkenyl" means any monovalent straight chain or branched chain hydrocarbon group containing one or more carbon-carbon double bonds where the site of attachment of the group can be either at a carbon-carbon double bond or elsewhere therein; and, the term "alkynyl" means any monovalent straight chain or branched chain hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein.

Representative examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The term "cycloalkyl" means any monovalent cyclic aliphatic hydrocarbon group; the term "cycloalkenyl" means any monovalent cyclic aliphatic hydrocarbon group containing one or more carbon-carbon double bonds where the site of attachment of the group can be either at a carbon-carbon double bond or elsewhere therein; and, the term "cycloalkynyl" means any monovalent cyclic aliphatic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein.

Representative examples of cycloalkyl include cyclopentyl, cyclobutyl, cyclopentyl, cycloheptyl, cyclooctyl. Examples of cyloalkenyl include cyclopentenyl, cycloheptenyl and cyclooctatrienyl. An example of cycloalkynyl is cycloheptynyl.

The terms "cycloalkyl", "cycloalkenyl", and "cycloalkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

Other than in the working examples, or where otherwise indicated, all numbers expressing amounts of materials, reaction conditions, time durations, quantified properties of materials, and so forth, stated in the specification and claims are to be understood as being modified in all instances by the term "about".

Useful hydrocarbyl groups include alkyl groups examples of which are methyl, ethyl, n-propyl, isopropyl, n-butyl, isobutyl, tert-butyl, n-pentyl, isopentyl, neopentyl and tertpentyl; hexyl such as n-hexyl; heptyl such as n-heptyl; octyl such as n-octyl, isooctyl and 2,2,4-trimethylpentyl; nonyl such as n-nonyl; decyl such as n-decyl; and cycloalkyl, such as cyclopentyl, cyclohexyl, cycloheptyl and methylcyclohexyl. Examples of alkenyl groups include vinyl, propenyl, allyl and methallyl. Examples of cylcoalkenyl groups include cyclohexenyl, norbornenyl, ethylnorbornenyl, ethylidenyl norbornane, ethylidene norbornyl, ethylidenylnorbornene and ethylidene norbornenyl. Examples of alkynyl groups include acetylenyl, propargyl and methylacetylenyl. Examples of aryl groups include phenyl, naphthyl; o-, m- and p-tolyl, xylyl, ethylphenyl and benzyl.

Among the more common known methods of producing imino-functional silanes are those involving the condensation reaction of amino-functional silane and a carbonyl compound, i.e., an aldehyde and/or ketone, either of which may contain additional functionality such as a secondary amino, hydroxyl or sulfhydryl group. The reaction splits out water which is advantageously collected as it forms. Upon completion of the reaction, excess reactant(s) are removed advantageously from the product imino-functional silane, for example, by distillation under vacuum. These reactions may be catalyzed by acids and/or bases.

Other methods of producing imino-functional silanes are those involving the reactions of imino-functional compounds that do not contain a silyl group with aminofunctional silanes. The reactions produce imino-functional silanes and the byproduct amines, which do not contain a silyl group. These reactions may be catalyzed by acids and/or bases.

In one embodiment of the present invention, the imino-functional silane to be treated is an imino-functional silane of general formula (I):

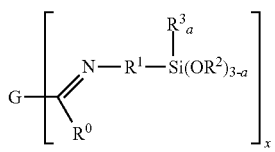

wherein:

$R^0$ is hydrogen, a monovalent hydrocarbon group of from 1 to about 20 carbon atoms such as an alkyl, cycloalkyl, aryl, alkaryl or aralkyl, group containing up to about 20 carbon atoms, or a monovalent heterocarbon group of from 1 to about 20 carbon atoms containing one or more heteroatoms such as N, O and/or S, specifically a hydrogen, a straight chain alkyl group of from 1 to about 10 carbon atoms, more specifically from 2 to 4 carbon atoms, e.g., ethyl, propyl or butyl, or a branched alkyl group of from 3 to about 10 carbon atoms, more specifically from 3 to about 6 carbon atoms and still more specifically 3 or 4 carbon atoms, e.g., isopropyl or isobutyl;

$R^1$ is a divalent hydrocarbon group of from 1 to about 20 carbon atoms such as alkylene, cycloalkylene, arylene, alkarylene or aralkylene, group containing up to about 20 carbon atoms or a divalent heterocarbon group of from 1 to about 20 carbon atoms containing one or more heteroatoms such as N, O and/or S, specifically a straight chain alkylene group of from 1 to about 10 carbon atoms, more specifically 2 to about 4 carbon atoms, e.g., ethylene, propylene or butylene, or a branched chain alkylene group of from 2 to about 10 carbon atoms, more specifically from 2 to about 6 carbon atoms and still more specifically 3 or 4 carbon atoms, e.g., isopropylene or isobutylene;

$R^2$ is an alkyl group of from 1 to about 5 carbon atoms, e.g., methyl, ethyl, propyl, isopropyl, butyl, isobutyl, pentyl or isopentyl;

$R^3$ is phenyl or an alkyl group of from 1 to about 8 carbon atoms, specifically methyl or ethyl;

G is a monovalent or polyvalent hydrocarbon group of from 1 to about 30 carbon atoms or a heterocarbon group of from 1 to about 30 carbon atoms containing one or more heteroatoms such as N, O and/or S, specifically a straight chain alkyl group of from 1 to about 10 carbon atoms, more specifically from 2 to 4 carbon atoms, e.g., ethyl, propyl or butyl, a substituted alkyl group containing from 1 to about 10 carbon atoms and one or more heteroatoms such as N, O and/or S, a branched chain alkyl group of from 3 to about 10 carbon atoms, more specifically from 3 to about 6 carbon atoms and still more specifically 3 or 4 carbon atoms, a substituted branched alkyl group of from 3 to about 10 carbon atoms containing one or more heteroatoms such as N, O and/or S, a cycloalkyl group of from 3 to about 10 carbon atoms, more specifically from about 5 to about 8 carbon atoms, e.g. cyclopentyl, cyclohexyl, cycloheptyl or cyclooctyl, an aryl group of from about 6 to about 10 carbon atoms, an arenyl group of from about 7 to about 10 carbon atoms, an aralkyl group of from about 7 to about 10 carbon atoms, a straight chain alkylene group of from 1 to about 10 carbon atoms, more specifically from 2 to 4 carbon atoms, e.g., ethylene, propylene or butylene, or a branched chain alkylene group of from 2 to about 10 carbon atoms, more specifically from 2 to about 6 carbon atoms and still more specifically 3 or 4 carbon atoms, a cycloalkylene group of from 3 to about 10 carbon atoms, more specifically from about 5 to about 8 carbon atoms, e.g., cyclopentylene, cyclohexylene, cycloheptylene or cyclooctylene, an arylene group of from about 6 to about 10 carbon atoms, an arenylene group of from about 7 to about 10 carbon atoms or an aralkylene group of from about 7 to about 10 carbon atoms;

subscript a is 0, 1 or 2, specifically 1; and, subscript x is 1, 2, 3 or 4, specifically 1 or 2 and more specifically 1.

Imino-functional silane (I) can be obtained by the reaction in a known manner, e.g., as described in U.S. Pat. No. 7,906,673, the entire contents of which are incorporated by reference herein, of amino-functional silane of general formula (II):

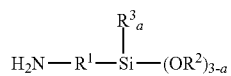

in which $R^1$, $R^2$ and $R^3$ and subscript a have the aforestated meanings, with a carbonyl-containing compound of general formula (III):

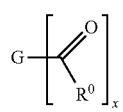

in which G, $R^0$ and subscript x have the aforestated meanings, the product imino-functional silane (I) being recovered employing any conventional or otherwise known technique(s), e.g., such as those described in aforementioned U.S. Pat. No. 7,906,673.

In another embodiment of the present invention, the imino-functional silane to be treated is an aldimino-functional silane of general formula (IV):

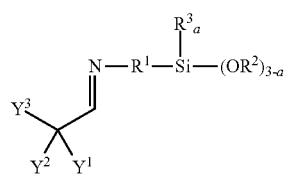

wherein:

$R^1$ is a divalent hydrocarbon group of up to about 20 carbon atoms or a divalent heterocarbon group of up to about 20 carbon atoms containing one or more heteroatoms such as N, O and/or S, specifically a straight chain alkylene group of from 1 to about 10 carbon atoms, more specifically from 2 to 4 carbon atoms, e.g., ethylene, propylene or butylene, or a branched chain alkylene group of from 2 to about 10 carbon atoms, more specifically from 2 to about 6 carbon atoms and still more specifically 3 or 4 carbon atoms, e.g., isopropylene or isobutylene;

$R^2$ is an alkyl group of from 1 to about 5 carbon atoms, e.g., methyl, ethyl, propyl, isopropyl, butyl, isobutyl, pentyl or isopentyl;

$R^3$ is phenyl or an alkyl group of from 1 to about 8 carbon atoms, specifically methyl or ethyl;

$Y^1$ and $Y^2$ each independently is hydrogen, an organic radical or together with the carbon atom to which they are bonded form a carbocyclic or heterocyclic ring of from about 5 to about 8, and specifically, 6, ring atoms;

$Y^3$ is a hydrogen, an unsubstituted or substituted alkyl group containing one or more heteroatoms such as N, O and/or S, an unbranched or branched alkyl or alkylenyl group of up to about 10 carbon atoms, a substituted or unsubstituted aryl or arylalkyl group of up to about 20 carbon atoms, specifically from about 6 to about 12 carbon atoms and still more specifically from about 6 to about 8 carbon atoms, or an —$OR^4$, —$OC(=O)$—$R^4$, —$C(=O)OR^4$ or —$C(=O)R^4$ group in which $R^4$ is an unsubstituted or substituted alkyl group of from 3 to about 20 carbon atoms, specifically from 3 to about 10 carbon atoms and more specifically from 3 to about 6 carbon atoms, or an unsubstituted or substituted aryl or aralkyl group of up to about 20 carbon atoms, specifically from about 6 to about 12 carbon atoms and still more specifically from about 6 to about 8 carbon atoms; and, subscript a is 0, 1 or 2

Aldimino-functional silane (IV) can be obtained by the reaction in a known manner, e.g., as described in aforementioned U.S. Pat. No. 7,906,673, of amino-functional silane of general formula (II):

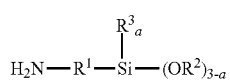

(II)

in which $R^1$, $R^2$ and $R^3$ and subscript a have the aforestated meanings, with aldehyde of general formula (V):

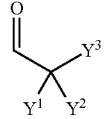

(V)

in which $Y^1$, $Y^2$ and $Y^3$ have the aforestated meanings, the product aldimino-functional silane (V) being recovered employing any conventional or otherwise known technique(s), e.g., such as those described in aforementioned U.S. Pat. No. 7,906,673.

In yet another embodiment of the present invention, the imino-functional silane to be treated is an aldimino-functional silane of general formula (VI):

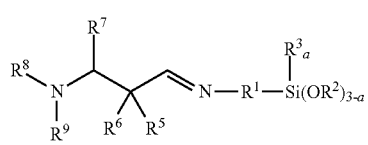

(VI)

wherein:

$R^1$, $R^2$, $R^3$ and subscript a have the aforestated meanings for aldimino-functional silane (IV);

$R^5$ and $R^6$ each independently is hydrogen, a monovalent hydrocarbon group of from 1 to about 12 carbon atoms or together with the carbon atom to which they are bonded form an unsubstituted or substituted ring of from about 5 to about 12 carbon atoms, specifically from about 5 to about 8 carbon atoms and more specifically, 5 or 6 carbon atoms, or a heterocarbon group containing from 1 to about 12 carbon atoms and one or more heteroatoms such as N, O and/or S;

$R^7$ is hydrogen, a monovalent hydrocarbon group such as an alkyl, cycloalkyl, aryl, alkaryl or aralkyl group of up to about 20 carbon atoms, more specifically up to about 12 carbon atoms and more specifically up to about 6 carbon atoms, a heterocarbon group containing up to about 20 carbon atoms and one or more heteroatoms such as N, O and/or S, or an alkoxycarboxyl group of from 2 to about 20 carbon atoms, specifically from 2 to about 12 carbon atoms and more specifically from 2 to about 6 carbon atoms; and, $R^8$ and $R^9$ each independently is a monovalent hydrocarbon group such as an alkyl, cycloalkyl, aryl, alkaryl or aralkyl group of up to about 20 carbon atoms, more specifically up to about 12 carbon atoms and more specifically up to about 6 carbon atoms, a heterocarbon group containing up to about 20 carbon atoms and one or more heteroatoms such as N, O and/or S, or an alkoxycarboxyl group of from 2 to about 20 carbon atoms, specifically from 2 to about 12 carbon atoms and more specifically from 2 to about 6 carbon atoms, or $R^8$ and $R^9$ and the carbon atom to which they are bonded form an unsubstituted or substituted ring of from about 5 to about 12 carbon atoms containing zero, one or more heteroatoms such as N, O and/or S.

Aldimino-functional silane (VI) can be obtained by the reaction in a known manner, e.g., as described in U.S. Pat. No. 8,877,955, the entire contents of which are incorporated by reference herein, of aminosilane (II), supra, as described above with aldehyde of general formula (VII):

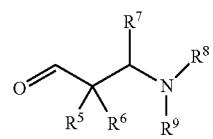

(VII)

in which $R^5$, $R^6$, $R^7$, $R^8$ and $R^9$ have the aforestated meanings of the aldimino-functional silane (VI), the product aldimino-functional silane (VI) being recovered employing any conventional or otherwise known technique(s), e.g., such as those described in aforementioned U.S. Pat. No. 8,877,955.

In yet another embodiment of the present invention, the imino-functional silane to be stabilized by the method of the invention is a ketimino-functional silane of general formula (VIII):

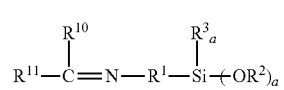

(VIII)

wherein:

$R^1$, $R^2$, $R^3$ and subscript a each have one of the same meanings stated above for aldimino-functional silane (IV);

$R^{10}$ and $R^{11}$ each independently is a monovalent hydrocarbon group of up to about 20 carbon atoms, specifically up to about 12 carbon atoms and still more specifically up to about 6 carbon atoms, or a monovalent heterocarbon group of up to about 20 carbon atoms, specifically up to about 12 carbon atoms and still more specifically up to about 6 carbon atoms, containing one or more heteroatoms such as N, O and/or S; and, subscript a is 0, 1 or 2.

Ketimino-functional silane (VIII) can be obtained by the reaction in a known manner, e.g., as described in U.S. Pat. No. 7,923,572, the entire contents of which are incorporated by reference herein, of amino-functional silane (II), supra, as described above with a ketone of general formula (IX):

(IX)

in which $R^{10}$ and $R^{11}$ have the aforestated meanings, the product ketimino-functional silane (VIII) being recovered employing any conventional or otherwise known technique(s), e.g., such as those described in aforementioned U.S. Pat. No. 7,923,572.

Representative and non-limiting examples of amino-functional silanes (II) that can be used to prepare imino-functional silane (I), aldimino-functional silanes (IV) and (VI) and ketimino-functional silane (VIII) include 3-aminopropyltrimethoxysilane, 3-aminopropyldimethoxymethylsilane, 3-amino-2-methylpropyltrimethoxysilane, 4-aminobutyltrimethoxysilane, 4-aminobutyldimethoxymethylsilane, 4-amino-3-methylbutyltrimethoxysilane, 4-amino-3,3-dimethylbutyltrimethoxysilane, 4-amino-3,3-dimethylbutyldimethoxymetyylsilane, 2-aminoethyltrimethoxysilane, 2-aminoethyldimethoxymethylsilane, aminomethyltrimethoxysilane, aminomethyldimethoxymethylsilane, aminomethylmethoxydimethylsilane, 7-amino-4-oxaheptyldimethoxymethylsilane as well as their analogs possessing ethoxy, propoxy or isopropoxy groups on the silicon atom; so-called diaminosilanes which in addition to a primary amino group possess a secondary amino group (—NH group) which, for example, is in the gamma position relative to the silicon atom, for example, N-(2-aminoethyl)-3-aminopropyltrimethoxysilane, N-(2-aminoethyl)-3-aminopropylmethyldimethoxysilane, N-(2-aminoethyl)-3-aminopropyltriethoxysilane and N-(2-aminoethyl)-3-aminopropyltriisopropoxysilane; and so-called triaminosilanes, which carry besides a primary amino group, two secondary amino groups (—NH groups) such as N-(2-aminoethyl)-N'-[3-(trimethoxysilyl)propyl]ethylenediamine.

Representative and non-limiting examples of carbonyl compounds (III) that can be used to prepare imino-functional silane (I) include formaldehyde, acetaldehyde, propionaldehyde, butyraldehyde, isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, phenylacetaldehyde, 2-methyl-3-phenylpropionaldehyde, 2-phenylpropionaldehyde, and diphenylacetaldehyde, 2,2-dimethyl-3-methylaminopropanal, 2,2-dimethyl-3-dimethylaminopropanal, 2,2-dimethyl-3-ethylaminopropanal, 2,2-dimethyl-3-diethylaminopropanal, 2,2-dimethyl-3-bis(2-methoxyethyl)aminopropanal, 2,2-dimethyl-3-butylaminopropanal, 2,2-dimethyl-3-dibutylaminopropanal, 2,2-dimethyl-3-hexylaminopropanal, 2,2-dimethyl-3-(2-ethylhexyl)aminopropanal, 2,2-dimethyl-3-dodecylaminopropanal, 2,2-dimethyl-3-(N-pyrrolidino)propanal, 2,2-dimethyl-3-(N-piperidino)propanal, 2,2-dimethyl-3-(N-morpholino)propanal, 2,2-dimethyl-3-(N-(2,6-dimethyl)morpholino)propanal, 2,2-dimethyl-3-benzylaminopropanal, 2,2-dimethyl-3-(N-benzylmethylamino)propanal, 2,2-dimethyl-3-(N-benzylisopropylamino)propanal, 2,2-dimethyl-3-cyclohexylaminopropanal and 2,2-dimethyl-3-(N-cyclohexylmethylamino)propanal, 4-oxo-pentanal, acetone, methylethylketone, methylpropylketone, methylisopropylketone, methylisobutylketone, dimethylketone, diethyl ketone, dipropylketone, diisopropylketone, dibutylketone and diisobutylketone, cyclopentanone, triemethylcyclopentanone, cyclohexanone, trimethylcyclohexanone, 6-oxo-2-heptanone, 5-oxo-2-hexanone, 1,4-diacetylbenzene, 1,3,5-triacetylbenzene and acetylacetone.

Representative and non-limiting examples of aldehydes (V) that can be used to prepare aldimino-functional silane (VI) include ethers of beta-hydroxyaldehydes as formed from a crossed aldol reaction from formaldehyde and a second aldehyde such as 2-methylbutyraldehyde, 2-ethylbutyraldehyde, 2-methylvaleraldehyde, 2-ethylcaproaldehyde, cyclopentane-carboxaldehyde, cyclohexanecarboxaldehyde, 1,2,3,6-tetrahydrobenz-aldehyde, 2-methyl-3-phenylpropionaldehyde, 2-phenylpropionaldehyde (hydratropaldehyde), and diphenylacetaldehyde, and alcohols such as methanol, ethanol, propanol, isopropanol, butanol, 2-ethylhexanol or fatty alcohols, such as, for example, 3-methoxy- and 3-ethoxy- and 3-propoxy- and 3-isopropoxy- and 3-butoxy-, and also 3-(2-ethylhexoxy)-2,2-dimethylpropanal; products of an esterification of the aforementioned β-hydroxyaldehydes such as 3-hydroxypivalaldehyde, 3-hydroxyisobutyraldehyde, 3-hydroxypropionaldehyde, 3-hydroxybutyraldehyde, 3-hydroxyvaleraldehyde, 2-hydroxymethyl-2-methyl-butyraldehyde, 2-hydroxymethyl-2-ethylbutyraldehyde, 2-hydroxymethyl-2-methylvaleraldehyde, 2-hydroxymethyl-2-ethylhexanal, 1-hydroxymethyl-cyclopentanecarbaldehyde, 1-hydroxymethylcyclohexanecarbaldehyde, 1-hydroxymethylcyclohex-3-enecarbaldehyde, 2-hydroxymethyl-2-methyl-3-phenylpropionaldehyde, 3-hydroxy-2-methyl-2-phenylprop- ionaldehyde and 3-hydroxy-2,2-diphenylpropionaldehyde with carboxylic acids such as formic acid, acetic acid, propionic acid, butyric acid, isobutyric acid, 2-ethylcaproic acid, and benzoic acid; and, esterification products of the aforementioned beta-hydroxyaldehydes such as 3-hydroxy-pivalaldehyde, 3-hydroxyisobutyraldehyde, 3-hydroxypropanal, 3-hydroxy-butyraldehyde, 3-hydroxyvaleraldehyde, 2-hydroxymethyl-2-methyl-butyraldehyde, 2-hydroxymethyl-2-ethylbutyraldehyde, 2-hydroxymethyl-2-methylvaleraldehyde, 2-hydroxymethyl-2-ethylhexanal, 1-hydroxymethyl-cyclopentanecarbaldehyde, 1-hydroxymethylcyclohexanecarbaldehyde, 1-hydroxymethylcyclohex-3-enecarbaldehyde, 2-hydroxymethyl-2-methyl-3-phenylpropionaldehyde, 3-hydroxy-2-methyl-2-phenylpropionaldehyde, and 3-hydroxy-2,2-diphenylpropionaldehyde with carboxylic acids such as, for example, lauric acid, tridecanoic acid, myristic acid, pentadecanoic acid, palmitic acid, margaric acid, stearic acid, nonadecanoic acid, arachidic acid, palmitoleic acid, oleic acid, erucic acid, linoleic acid, linolenic acid, eleostearic acid, arachidonic acid, succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydro-terephthalic acid, 3,6,9-trioxaundecanedioic acid, and similar derivatives of polyethylene glycol, dehydrogenated ricinoleic acids, and also fatty acids from the industrial saponification of natural oils and fats such as, for example, rapeseed oil, sunflower oil, linseed oil, olive oil, coconut oil, oil-palm kernel oil, and oil-palm oil.

Representative and non-limiting examples of aldehydes (VII) that can be used to prepare aldimino-functional silane (VI) include 2,2-dimethyl-3-methylaminopropanal, 2,2-dimethyl-3-dimethylaminopropanal, 2,2-dimethyl-3-ethylaminopropanal, 2,2-dimethyl-3-diethylaminopropanal, 2,2-dimethyl-3-bis(2-methoxyethyl)aminopropanal, 2,2-dimethyl-3-butylaminopropanal, 2,2-dimethyl-3-dibutylaminopropanal, 2,2-dimethyl-3-hexylaminopropanal, 2,2-dimethyl-3-(2-ethylhexyl)aminopropanal, 2,2-dimethyl-3-dodecylaminopropanal, 2,2-dimethyl-3-(N-pyrrolidino)propanal, 2,2-dimethyl-3-(N-piperidino)propanal, 2,2-dimethyl-3-(N-morpholino)propanal, 2,2-dimethyl-3-(N-(2,6-dimethyl)morpholino)propanal, 2,2-dimethyl-3-benzylaminopropanal, 2,2-dimethyl-3-(N-benzylmethylamino)propanal, 2,2-dimethyl-3-(N-benzylisopropylamino)propanal, 2,2-dimethyl-3-cyclohexylaminopropanal and 2,2-dimethyl-3-(N-cyclohexylmethylamino)propanal.

Representative and non-limiting examples of ketones (IX) that can be used to prepare ketiminosilanes (VIII) include aliphatic ketones such as acetone, methylethylketone, methylpropylketone, methylisopropylketone, methylisobutylketone, dimethylketone, diethyl ketone, dipropylketone, diisopropylketone, dibutylketone and diisobutylketone, and cyclic ketones such as cyclopentanone, triemethylcyclopentanone, cyclohexanone and trimethylcyclohexanone.

In one particular embodiment, the method of stabilizing imino-functional silane in accordance with the invention comprises:

a) adding a Brønsted-Lowry base to an imino-functional silane that is susceptible to undergoing self-addition and deamination reactions resulting from the presence therein of a proton source; and, b) mixing the imino-functional silane with the Brønsted-Lowry base thereby neutralizing the proton source and providing stabilized imino-functional silane.

In the aforedescribed embodiment of the method of the invention, the Brønsted-Lowry base added to the imino-functional silane in step (a) should be sufficient to inhibit self-addition and deamination reactions of the imino-functional silane. In one embodiment, such amount of Brønsted-Lowry base will generally be at least about 1 molar equivalent, more specifically from about 1 to about 10 molar equivalents and even more specifically from about 1.2 to about 10 molar equivalents, based on the moles of proton source present in the imino-functional silane.

The foregoing embodiment may additionally comprise:

c) separating the Brønsted-Lowry base from the mixture of imino-functional silane and Brønsted-Lowry base of step (b) to provide a stabilized, imino-functional silane, preferably one that is substantially free of Brønsted-Lowry base; and, d) collecting the stabilized imino-functional silane of step (c).

It will be appreciated that the selected Brønsted-Lowry base must be sufficiently basic to neutralize the proton source. In one embodiment, the conjugate acid of the Brønsted-Lowry base use to neutralize the proton source will have a pKa in water of greater than about 12, specifically a pKa of from about 12 to about 25, and more specifically a pKa of from about 13 to about 20. The pKa values for the conjugate acid of the Brønsted-Lowry base can be found in, inter alia, "Advanced Organic Chemistry", 3rd ed., J. March (1985) and in references cited therein, and in "CRC Handbook of Chemistry and Physics", David R. Lide, editor, 72 ed. (CRC Press 1991-92). Such pKa values can also be determined by the method of R. G. Bates and G. D. Pinching, *J. Am., Chem. Soc.*, 72, 1393 (1950) at 25° C. The Brønsted-Lowry base will have sufficient basicity if it is a hydroxide, alkoxide or oxide of an alkali or alkaline metal.

As used herein, the expression "substantially free of Brønsted-Lowry base" shall be understood to mean a stabilized imino-functional silane containing less than about 1 weight percent, specifically less than about 0.01 weight percent, more specifically less than about 0.0001 weight percent, and still more specifically from about 0.0001 to about 0.1 weight percent, Brønsted-Lowry base based on the weight of the stabilized imino-functional silane.

In one embodiment, the amount of Brønsted-Lowry base in the stabilized imino-functional silane may be determined using Inductively Coupled Plasma Mass Spectrometry.

In one embodiment, a stabilized imino-functional silane is an imino-functional silane containing less than about 2 weight percent conjugated carbon-carbon double bond-containing imino-functional silane based on the total weight of conjugated carbon-carbon double bond-containing imino-functional silane and imino-functional silane after storage (aging) at 25° C. for 4 weeks. More specifically, a stabilized imino-functional silane is an imino-functional silane that contains less than about 0.5 weight percent conjugated carbon-carbon double bond-containing imino-functional silane, and still more specifically, less than 0.1 weight percent of conjugated carbon-carbon double bond-containing imino-functional silane, based on the total weight of conjugated carbon-carbon double bond-containing imino-functional silane and imino-functional silane after storage at 25° C. for 4 weeks.

In another embodiment, the stabilized imino-functional silane contains less than about 15 ppm, specifically less than about 1 ppm, proton source based on the weight of the imino-functional silane.

In one embodiment, the weight percent of the conjugated carbon-carbon double bond-containing imino-functional silane in the stabilized imino-functional silane can be determined employing gas chromatography (GC) using dodecane as an internal standard. In accordance with one GC procedure, the GC column is 30 meters long and 0.25 millimeters in diameter and coated with a 0.25 micron film (HP-5 from Agilent), the flow of helium carrier gas is 1 mL per minute, with an initial temperature profile of 50° C. for 2 minutes followed by an increase of 8° C. per minute up to a temperature of 340° C., holding at the latter temperature for 5 minutes, and using a flame ionization detector (FID).

As indicated above, even trace amounts of acidic proton will result in undesirable addition and deamination reactions of imino-functional silane. The proton source present in the iminosilane can come from a variety of sources, for example, as residual acid(s) associated with one or more of the amino-functional silane, aldehyde and/or ketone reactants and may even result from absorption of atmospheric carbon dioxide and water by the imino-functional silane.

Neutralization of the proton source can be achieved by the addition of a suitable amount of at least one Brønsted-Lowry base to the proton source-containing imino-functional silane. In one embodiment, a suitable amount of the at least one Brønsted-Lowry base is at least 1 molar equivalent, more specifically from about 1 to about 10 molar equivalents and even more specifically from about 1.2 to about 10 molar equivalents, based on the moles of proton source present in the imino-functional silane.

In one embodiment, the Brønsted-Lowry base is a compound having the general formula (X):

wherein M is an alkali metal or alkaline earth metal and R is hydrogen, a hydrocarbon group of from 1 to about 20 carbon atoms, a heterocarbon group of up to about 20 carbon atoms, specifically from 1 to about 12 carbon atoms and still more specifically from 1 to about 6 carbon atoms, a p-orbital of the oxygen atom containing a lone paired electrons, or M, and subscript f is 1 or 2, with the provisos that (i) when M is an alkali metal, then subscript f is 1; (ii) when M is an alkaline earth metal, then subscript f is 2, except when R is a p-orbital of oxygen atom containing a lone pair of electrons; (iii) when R is M, then M is an alkali metal; and (iv) when R is a p-orbital of the oxygen atom containing a lone pair of electrons, then M is an alkaline metal and subscript f is 1. It is understood that the Brønsted-Lowry base of formula (X) is a salt of an alkali or alkaline hydroxide, alkoxide or oxide.

In another embodiment, in a preferred group of Brønsted-Lowry bases (X), M is an alkali or alkaline earth metal, R is hydrogen or a hydrocarbon group of from 1 to about 20 carbon atoms, specifically from 1 to about 12 carbon atoms, more specifically from 1 to about 6 carbon atoms, and still more specifically methyl or ethyl, and subscript f is 1 or 2 with the provisos that when M is an alkali metal, subscript f is 1 and when M is an alkaline earth metal, subscript f is 2.

Representative and non-limiting examples of Brønsted-Lowry base (X) that can be used for this purpose include alkali metal and alkaline metal hydroxides, alkoxides and oxides such as LiOH, NaOH, KOH, CsOH, Mg(OH)$_2$, Ca(OH)$_2$, Ba(OH)$_2$, NaOMe, KOMe, NaOEt, KOEt, CaO, MgO, BaO and any combinations thereof.

The amount of Brønsted-Lowry base (X) added to the imino-functional silane to be stabilized will generally range from about 0.0001 to about 10 weight percent, specifically from about 0.001 to about 5 weight percent, and more specifically from about 0.1 to about 1 weight percent, based upon the total weight of the imino-functional silane and Brønsted-Lowry base.

In one embodiment of the invention, the selected Brønsted-Lowry base is one that is soluble in the imino-functional silane at the concentration employed and matches the alkoxy functionality of the silane moiety of the imino-functional silane, for example, sodium methoxide in the case of trimethoxysilane-functional iminosilane, sodium ethoxide in the case of triethoxysilane-functional iminosilane, etc.

Neutralization of the proton source can be carried out before, during or after distillation of the imino-functional silane reaction medium to recover any unreacted aminosilane, aldehyde and/or ketone reactant(s). However, in general, it is preferred to add the neutralizing Brønsted-Lowry base to the imino-functional silane during or immediately after such distillation and more preferred, during distillation where the imino-functional silane is distilled from a mixture of the imino-functional silane and the Brønsted-Lowry base (X).

In embodiments of the present invention, separation of Brønsted-Lowry base and/or Brønsted-Lowry acid can be achieved either by distillation of the treated imino-functional silane, i.e., a mixture of the imino-functional silane and Brønsted-Lowry base and/or Brønsted-Lowry acid, by extraction, by a preparatory chromatographic method, by filtration or by any other conventional or otherwise known separation method, as well as by a combination of two or more of such methods.

COMPARATIVE EXAMPLE 1

Preparation of Non-Stabilized 3-(1,3-Dimethylbutylidene) Aminopropyltriethoxysilane This example is provided for comparison purposes and illustrates a known process for preparing the ketiminosilane, 3-(1,3-dimethylbutylidene) aminopropyltriethoxysilane:

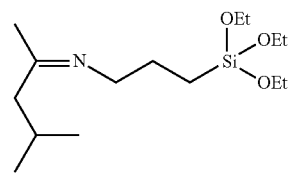 [SMILES: CCO[Si](CCC/N=C(/C)CC(C)C)(OCC)OCC]

Into a four neck round bottom flask (5 L) fitted with a Dean Stark trap and condenser, thermocouple, addition funnel and a stopper was added methylisobutylketone (MIBK) (3 L). The Dean Stark trap was filled with MIBK (~125 mL) and the head space of the reaction vessel was flushed with nitrogen. The MIBK was heated to reflux and gamma-aminopropyltriethoxysilane (593.08 g) was added drop wise to the refluxing MIBK over a period of four hours and fifteen minutes. The resulting reaction mixture was heated at reflux for an additional one hour after the completion of the aminosilane. Approximately 37 mL of water was collected in the Dean Stark trap during the course of the reaction. The reaction mixture was purified by distillation, first removing ~2.2 L of volatiles (MIBK and EtOH) at atmospheric pressure. The resulting crude 3-(1,3-dimethylbutylidene) aminopropyltriethyoxysilane was further purified via vacuum distillation.

EXAMPLE 1

Preparation of Stabilized 3-(1,3-Dimethylbutylidene) Aminopropyltriethoxysilane

To a three neck round bottom flask (1 L) fitted with a Dean Stark trap and condenser, thermocouple, and addition funnel was added MIBK (585 mL). The Dean Stark trap was filled with MIBK (~25 mL) and the head space of the reaction vessel was flushed with nitrogen. The MIBK was heated to reflux and gamma-aminopropyltriethoxysilane (100 mL) was added drop wise to the refluxing MIBK over a period of one hour and twenty five minutes. The resulting reaction mixture was heated at reflux for an additional one and a half hours after the completion of the aminosilane addition. Approximately 7 mL of water was collected in the Dean Stark trap during the course of the reaction. The reaction mixture was purified by distillation, first removing ~525 mL of volatiles (MIBK and EtOH) at atmospheric pressure. After removal of the lights, a 21 wt % solution of sodium ethoxide in ethanol (0.824 mL, 0.7156 g) was added to the crude (3-(1,3-dimethylbutylidene) aminopropyltriethyoxysilane). The crude product containing sodium ethoxide was further purified via vacuum distillation.

To demonstrate the improved storage stability of the iminosilane of Example 1 by comparison to that of Comparative Example 1, samples of both products were analyzed for purity by GC over the course of six weeks. Both materials were stored in ~20 mL glass vials with a Teflon lined cap, the head space was purged with nitrogen and the filled vials were stored in a dark cabinet to prevent deterioration by light. As shown in the table below, the iminosilane made by the method of Example 1 retained high purity over the course of six weeks in contrast to the product made by the method of Comparative Example 1 which lost approximately 2% product after 4 weeks of aging.

TABLE I

| Preparative Method | As Made | 1 week | 2 week | 4 week | 6 week |
|---|---|---|---|---|---|
| Comparative Example I | 98.87% | No Test | 97.90% | 96.97% | No Test |
| Example 1 | 99.20% | 99.35% | 99.47% | 99.41% | 99.57% |

EXAMPLES 2-12

Preparation of Imino-Functional Silanes

Employing substantially the same procedures as described in Example 1, imino-functional silanes can be prepared from the amines, ketones and aldehydes and stabilized by the addition of the Brønsted-Lowry bases indicated in Table II below:

was charged into the addition funnel. The reaction mixture was heated to reflux and N-butylamine was added drop wise to the refluxing methyl isobutyl ketone over a period of one hour and ten minutes. The resulting reaction mixture was heated at reflux for an additional one hour and ten minutes after the completion of the N-butylamine addition. Approximately 18 mL of water was collected in the Dean Stark trap during the course of the reaction. The Dean Stark trap and condenser were replaced with a 3" vigreux column and distillation head. Approximately 382 grams of volatiles, which were methyl isobutyl ketone and N-butylamine, were removed by vacuum stripping at a reduced pressed ranging from 280 to 420 mm Hg. After removal of the lights, an equal molar quantity of gamma-aminopropyltriethoxysilane was charged into the reaction mixture. N-butylamine was removed by vacuum at 55° C. and 140 mm Hg and the crude 3-(1,3-dimethylbutylidene) aminopropyltriethyoxysilane was filtered thru a 1 micron filter pad.

The crude 3-(1,3-dimethylbutylidene) aminopropyltriethoxysilane can be treated with a Brønsted-Lowry base during the distillation process.

EXAMPLE 14

Two-step Process for Preparing Crude Aldimino Adduct of Terephthalaldehyde and 3-Aminopropyltriethyoxysilane Into a four neck round bottom flask (5 L) fitted with a Dean Stark trap, condenser, thermocouple, addition funnel

TABLE II

| Ex. | Amine | Ketone/Aldehyde | Imine Product | Base |
|---|---|---|---|---|
| 2 | gamma-aminopropyltriethoxysilane | methylisobutylketone | (1,3-dimethyl-butylidene)-(3-triethoxy-silanyl-propyl)-amine | sodium ethoxide |
| 3 | gamma-aminopropyltrimethoxysilane | methylisobutylketone | (1,3-dimethyl-butylidene)-(3-trimethoxy-silanyl-propyl)-amine | sodium methoxide |
| 4 | 4-amino-3-dimethyl-1-butyltriethoxylsilane | methylisobutylketone | (1,3-dimethyl-butylidene)-(2,2-dimethyl-4-triethoxysilanyl-butyl)-amine | sodium ethoxide |
| 5 | gamma-aminopropylmethyl-diethoxysilane | acetone | isopropylidene-(3-methyl-diethoxy-silanyl-propyl)-amine | sodium ethoxide |
| 6 | gamma-aminopropyltriethoxysilane | methylethylketone | sec-butylidene-(3-triethoxy-silanyl-propyl)-amine | sodium ethoxide |
| 7 | gamma-aminopropyltriethoxysilane | acetophenone | [3-(triethoxy-silanyl)-propyl]-(1-phenyl-ethylidene)-amine | sodium ethoxide |
| 8 | gamma-aminopropyldimethylethoxy-silane | acetaldehyde | ethylidene-(3-dimethyl-ethoxy-silanyl-propyl)-amine | sodium ethoxide |
| 9 | gamma-aminopropyltriethoxysilane | isobutyraldehyde | (3-methyl-butylidene)-(3-triethoxy-silanyl-propyl)-amine | sodium ethoxide |
| 10 | gamma-aminopropyltriethoxysilane | benzaldehyde | benzylidene-(3-triethoxy-silanyl-propyl)-amine | sodium ethoxide |
| 11 | gamma-aminopropyltriethoxysilane | 3-dimethylamino-2,2-dimethyl-propionaldehyde | [2,2-dimethyl-3-(3-triethoxy-silanyl-propylimino)-propyl]-dimethyl-amine | sodium ethoxide |
| 12 | N-(2-aminoethyl)-3-aminopropyltrimethoxysilane | methylethylketone | N-sec-butylidene-N'-(3-trimethoxy-silanyl-propyl)-ethane-1,2-diamine | CaO |

EXAMPLE 13

Two-Step Process for Preparing Crude 3-(1,3-Dimethylbutylidene) Aminopropyltriethyoxysilane Into a four neck round bottom flask (1 L) fitted with a Dean Stark trap, condenser, thermocouple, addition funnel and mechanical stirrer was added methyl isobutyl ketone (502 grams, 5 moles). N-butylamine (73.14 grams, 1 mole)

and mechanical stirrer was added terephthalaldehyde (569 grams 4.24 moles) along with toluene (2,020 grams, 22 moles). N-butylamine (620 grams, 8.48 moles) was charged into the addition funnel. The reaction mixture was heated to reflux and N-butylamine was added drop wise to the refluxing mixture over 3 hour and forty-five minutes. Approximately 150 ml of water was collected during the course of the reaction. The Dean Stark trap and condenser were replaced with a vacuum distillation head. Approximately 1,777 grams of volatiles consisting of toluene and N-butylamine were removed by vacuum stripping at reduced pressures ranging from 18 to 150 mm Hg.

After removal of the lights, 3-aminopropyltriethoxysilane (2,061.5 grams, 9.33 moles) was charged into the reaction mixture. N-butylamine and excess 3-aminopropyltriethoxysialne were removed under reduced pressures ranging from 240 to 11 mm Hg with a reaction pot temperature between room temperature and 170° C. The crude aldiminosilane adduct was filtered thru a 1 micron filter pad.

The crude aldiminosilane adduct can be treated with a Brønsted-Lowry base during the distillation process.

EXAMPLE 15

Distillation of 3-(1,3-Dimethylbutylidene) Aminopropyltriethyoxysilane from Potassium Hydroxide Potassium hydroxide (0.1 gram) was added to 100 grams of 3-(1,3-dimethylbutylidene) aminopropyltriethoxysilane prepared in accordance with Comparative Example I. The mixture was purified via vacuum distillation at 108° C. at 1.57 mm Hg to yield a clear colorless solution. The purity of the product was 99.61 percent using GC. After aging for 14 days at 50° C., the purity of the aged product was 99.52 percent. The experiment illustrated that the product can be successfully distilled from potassium hydroxide.

EXAMPLE 16

Distillation of 3-(1,3-Dimethylbutylidene) Aminopropyltriethyoxysilane from Calcium Hydroxide Calcium hydroxide (0.11 gram) was added to 106.2 grams of 3-(1,3-dimethylbutylidene) aminopropyltriethoxysilane prepared in accordance with Comparative Example I. The mixture was purified via vacuum distillation at a temperature of 124° C. and pressure of 2.4 mm Hg to yield a clear colorless solution. The purity of the product was 99.34 percent using GC. The experiment illustrated that the product can be successfully distilled from calcium hydroxide.

EXAMPLE 17

Distillation of 3-(1,3-Dimethylbutylidene) Aminopropyltriethyoxysilane from Magnesium Oxide Magnesium oxide (0.10 gram) was added to 100 grams of 3-(1,3-dimethylbutylidene) aminopropyltriethoxysilane prepared in accordance with Comparative Example I. The mixture was purified via vacuum distillation at a temperature of 120° C. and pressure of 1.73 mm Hg to yield a clear colorless solution. The purity of the product was 99.57 percent using GC. The experiment illustrated that the product can be successfully distilled from calcium hydroxide.

EXAMPLE 18

Distillation of 3-(1,3-Dimethylbutylidene) Aminopropyltriethyoxysilane from Sodium Carbonate Sodium carbonate (anhydrous) (0.1 grams) was added to 100 grams of 3-(1,3-dimethylbutylidene) aminopropyltriethoxysilane prepared in accordance with Comparative Example I. The mixture was purified via vacuum distillation at a temperature of 107° C. and a pressure of 1.52 mm Hg to yield a clear colorless solution. The purity of the product was 99.71 percent using GC. This example illustrates that the product can be successfully distilled from sodium carbonate.

EXAMPLE 19

Preparation 3-(1-Octylidene) Aminopropyltrimethyoxysilane

The imino-functional silane

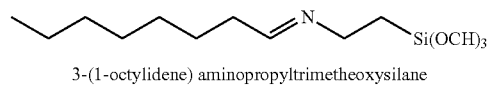

3-(1-octylidene) aminopropyltrimetheoxysilane was prepared as follows:

Into a four neck round bottom flask (2 L) fitted with a Dean Stark trap, condenser, thermocouple, addition funnel and mechanical stirrer was added octanal (96 grams, 0.75 mole) and toluene (800 grams, 8.68 moles). 3-Aminopropyltrimethoxysilane (169 grams, 0.94 mole) was charged into the addition funnel. The reaction mixture was heated to reflux and 3-aminopropyltrimethoxysilane was added drop wise to the refluxing toluene/octanal mixture over a period of two hour and twenty minutes. Approximately 16 mL of water was collected in the Dean Stark trap during the course of the reaction. The Dean Stark trap and condenser were replaced with a short path distillation head. Approximately 780 grams of volatiles, which included toluene and methanol, were removed by distillation at atmospheric pressure followed by vacuum stripping at 350 to 11 mm Hg). After removal of the lights, 1.1 grams of 25 wt % solution of sodium methoxide in methanol was added to 220 grams of crude 3-(1-octylidene) aminopropyltrimethyoxysilane and further purified via vacuum distillation at a temperature range of 126 to 141° C. and at a pressure of 1.45 mm Hg to yield a clear colorless solution.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended thereto.

The invention claimed is:

1. A stabilized imino-functional silane which contains less than about 15 ppm proton source based on the weight of the stabilized imino-functional silane and contains less than about 2 weight percent conjugated carbon-carbon double bond-containing imino-functional silane based on the total weight of conjugated carbon-carbon double bond-containing imino-functional silane and imino-functional silane after storage at 25° C. for 4 weeks and wherein the imino-functional silane is an imino-functional alkoxysilane of general formula (I):

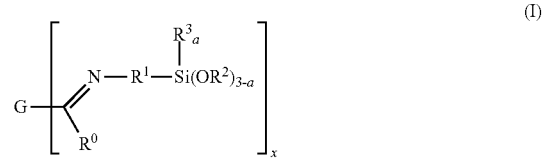

wherein:
R⁰ is hydrogen, a monovalent hydrocarbon group of from 1 to about 20 carbon atoms or a monovalent heterocarbon group of from 1 to about 20 carbon atoms containing one or more heteroatoms;
R¹ is a divalent hydrocarbon group of from 1 to about 20 carbon atoms or a divalent heterocarbon group of from 1 to about 20 carbon atoms;
R² is an alkyl group of from 1 to about 5 carbon atoms;
R³ is phenyl or an alkyl group of from 1 to about 8 carbon atoms;
G is a monovalent or polyvalent hydrocarbon group of from 1 to about 30 carbon atoms or a heterocarbon group of from 1 to about 30 carbon atoms containing one or more heteroatoms where the carbon of G which connects to the imino group is unsubstituted;
subscript a is 0, 1 or 2; and,
subscript x is 1 or 2.

2. The stabilized imino-functional silane of claim 1, wherein the stabilized imino-functional silane contains less than about 1 ppm proton source based on the weight of the imino-functional silane.

3. The stabilized imino-functional silane of claim 1, wherein the stabilized imino-functional silane contains less than about 0.1 weight percent conjugated carbon-carbon double bond-containing imino-functional silane based on the total weight of conjugated carbon-carbon double bond-containing imino-functional silane and contains less than about 1 ppm proton source based on the weight of the imino-functional silane.

4. The stabilized imino-functional silane of claim 1, wherein the imino-functional silane is at least one member selected from the group consisting of:
aldimino-functional silane of general formula (IV):

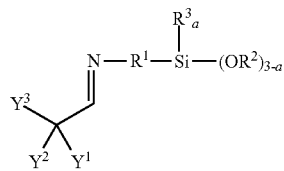

(IV)

wherein:
R¹ is a divalent hydrocarbon group of up to about 20 carbon atoms or a divalent heterocarbon group of up to about 20 carbon atoms containing one or more heteroatoms;
R² is an alkyl group of from 1 to about 5 carbon atoms;
R³ is phenyl or an alkyl group of from 1 to about 8 carbon atoms;
Y¹ and Y² are hydrogen;
Y³ is hydrogen, an unsubstituted or substituted alkyl group of up to about 10 carbon atoms containing one or more heteroatoms, an unbranched or branched alkyl or alkylenyl group of up to about 10 carbon atoms, a substituted or unsubstituted aryl or arylalkyl group of up to about 20 carbon atoms, or an —OR⁴, —OC(=O)—R⁴, —C(=O)OR⁴ or C(=O)R⁴ group in which R⁴ is an unsubstituted or substituted alkyl group of from 3 to about 20 carbon atoms; and,
subscript a is 0, 1 or 2, an aldimino-functional silane of general formula (VI):

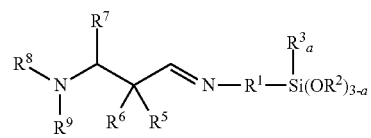

(VI)

wherein:
R¹, R², R³ and subscript a have the aforestated meanings for aldimino-functional silane (IV);
R⁵ and R⁶ are hydrogen;
R⁷ is hydrogen, a monovalent hydrocarbon group of up to about 20 carbon atoms, a heterocarbon group containing up to about 20 carbon atoms and one or more heteroatoms, or an alkoxycarboxyl group of from 2 to about 20 carbon atoms; and,
R⁸ and R⁹ each independently is a monovalent hydrocarbon group of up to about 20 carbon atoms, a heterocarbon group containing up to about 20 carbon atoms and one or more heteroatoms, or an alkoxycarboxyl group of from 2 to about 20 carbon atoms, or R⁸ and R⁹ and the carbon atom to which they are bonded form an unsubstituted or substituted ring of from about 5 to about 12 carbon atoms containing zero, one or more heteroatoms,
and a ketimino-functional silane of general formula (VIII):

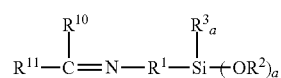

(VIII)

wherein:
R¹, R², R³ and subscript a each have one of the same meanings stated above for aldimino-functional silane (IV);
R¹⁰ and R¹¹ each independently is a monovalent hydrocarbon group of up to about 20 carbon atoms or a monovalent heterocarbon group of up to about 20 carbon atoms containing one or more heteroatoms where the carbon of R¹¹ which connects to the imino group is unsubstituted; and,
subscript a is 0, 1 or 2.

5. The stabilized imino-functional silane of claim 1, wherein the imino-functional silane is (1,3-dimethyl-butylidene)-(3-triethoxy-silanyl-propyl)-amine, (1,3-dimethyl-butylidene)-(3-trimethoxy-silanyl-propyl)-amine, (1,3-dimethyl-butylidene)-(2,2-dimethyl-4-triethoxysilanyl-butyl)-amine, isopropylidene-(3-methyl-diethoxy-silanyl-propyl)-amine, sec-butylidene-(3-triethoxy-silanyl-propyl)-amine, [3-(triethoxy-silanyl)-propyl]-(1-phenyl-ethylidene)-amine, ethylidene-(3-dimethyl-ethoxy-silanyl-propyl)-amine, (3-methyl-butylidene)-(3-triethoxy-silanyl-propyl)-amine, N sec-butylidene-N'-(3-trimethoxy-silanyl-propyl)-ethane-1,2-diamine or 3-(1-octylidene aminopropyltrimetheoxysilane.

6. The stabilized imino-functional silane of claim 1, further comprising a Brønsted-Lowry base.

7. The stabilized imino-functional silane of claim 6, wherein the amount of Brønsted-Lowry base added to the imino-functional silane is sufficient to inhibit self-addition and deamination reactions of the imino-functional silane.

8. The stabilized imino-functional silane of claim 6, wherein the amount of Brønsted-Lowry base added to the imino-functional silane is at least 1 molar equivalent based on the moles of proton source present in the imino-functional silane.

9. The stabilized imino-functional silane of claim 6, wherein the Brønsted-Lowry base is from about 0.0001 to about 0.1 weight percent, based on the weight of the imino-functional silane.

10. The stabilized imino-functional silane of claim 6, wherein the Brønsted-Lowry base is at least one member selected from the group consisting of alkali metal and alkaline metal hydroxides, alkoxides and oxides.

11. The stabilized imino-functional silane of claim 10, wherein the Brønsted-Lowry base is at least one member selected from the group consisting of LiOH, NaOH, KOH, CsOH, $Mg(OH)_2$, $Ca(OH)_2$, $Ba(OH)_2$, NaOMe, KOMe, NaOEt, KOEt, CaO, MgO and BaO.

12. The stabilized imino-functional silane of claim 6, wherein the imino-functional silane is (1,3-dimethyl-butylidene)-(3-triethoxy-silanyl-propyl)-amine, (1,3-dimethyl-butylidene)-(3-trimethoxy-silanyl-propyl)-amine, (1,3-dimethyl-butylidene)-(2,2-dimethyl-4-triethoxysilanyl-butyl)-amine, isopropylidene-(3-methyl-diethoxy-silanyl-propyl)-amine, sec-butylidene-(3-triethoxy-silanyl-propyl)-amine, [3-(triethoxy-silanyl)-propyl]-(1-phenyl-ethylidene)-amine, ethylidene-(3-dimethyl-ethoxy-silanyl-propyl)-amine, (3-methyl-butylidene)-(3-triethoxy-silanyl-propyl)-amine, N sec-butylidene-N'-(3-trimethoxy-silanyl-propyl)-ethane-1,2-diamine or 3-(1-octylidene aminopropyltrimetheoxysilane.

13. The stabilized imino-functional silane of claim 12, wherein the Brønsted-Lowry base is at least one member selected from the group consisting of LiOH, NaOH, KOH, CsOH, $Mg(OH)_2$, $Ca(OH)_2$, $Ba(OH)_2$, NaOMe, KOMe, NaOEt, KOEt, CaO, MgO and BaO.

14. The stabilized imino-functional silane of claim 13, wherein the Brønsted-Lowry base is from about 0.0001 to about 0.1 weight percent, based on the weight of the imino-functional silane.

15. A stabilized imino-functional silane which contains less than about 15 ppm proton source based on the weight of the stabilized imino-functional silane and contains less than about 0.5 weight percent conjugated carbon-carbon double bond-containing imino-functional silane based on the total weight of conjugated carbon-carbon double bond-containing imino-functional silane and imino-functional silane after storage at 25° C. for 4 weeks and wherein the imino-functional silane is an imino-functional alkoxysilane of general formula (I):

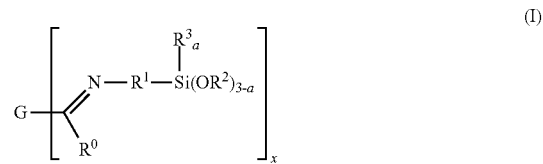

wherein:
R⁰ is hydrogen, a monovalent hydrocarbon group of from 1 to about 20 carbon atoms or a monovalent heterocarbon group of from 1 to about 20 carbon atoms containing one or more heteroatoms;
R¹ is a divalent hydrocarbon group of from 1 to about 20 carbon atoms or a divalent heterocarbon group of from 1 to about 20 carbon atoms;
R² is an alkyl group of from 1 to about 5 carbon atoms;
R³ is phenyl or an alkyl group of from 1 to about 8 carbon atoms;
G is a monovalent or polyvalent hydrocarbon group of from 1 to about 30 carbon atoms or a heterocarbon group of from 1 to about 30 carbon atoms containing one or more heteroatoms where the carbon of G which connects to the imino group is unsubstituted;
subscript a is 0, 1 or 2; and,
subscript x is 1 or 2.

* * * * *